United States Patent [19]

Wang

[11] Patent Number: 4,702,260
[45] Date of Patent: Oct. 27, 1987

[54] FLEXIBLE BRONCHOSCOPIC NEEDLE ASSEMBLY

[76] Inventor: Ko Pen Wang, 1106 Nacirema La., Stevenson, Md. 21153

[21] Appl. No.: 723,907
[22] Filed: Apr. 16, 1985
[51] Int. Cl.$^4$ ............................................. A61B 10/00
[52] U.S. Cl. ..................................... 128/753; 128/751; 128/305; 604/264; 604/272
[58] Field of Search ............... 604/158, 161, 163, 165, 604/164, 264, 93, 51, 53, 272–274; 128/751, 753, 754, 749, 305, 312

[56] References Cited

U.S. PATENT DOCUMENTS

| 387,454 | 8/1888 | Siegenthaler | 604/272 |
|---|---|---|---|
| 1,585,934 | 5/1926 | Muir | 128/754 |
| 2,623,521 | 12/1952 | Shaw | 128/753 |
| 2,828,744 | 4/1958 | Hirsch et al. | 604/272 |
| 2,919,692 | 1/1960 | Ackermann | 128/754 |
| 2,989,053 | 6/1961 | Hamilton | 604/274 |
| 3,587,560 | 6/1971 | Glassman | 128/753 |
| 3,605,721 | 9/1971 | Hallac | 128/754 |
| 3,659,610 | 5/1972 | Cimber | 604/162 |
| 3,776,239 | 12/1973 | Cooley | 604/272 |
| 4,230,123 | 10/1980 | Hawkins, Jr. | 128/754 |
| 4,396,021 | 8/1983 | Baumgartner | 128/754 |
| 4,461,280 | 7/1984 | Baumgartner | 604/51 |
| 4,532,935 | 8/1985 | Wang | 128/753 |
| 4,555,243 | 11/1985 | Markham | 604/272 |

Primary Examiner—C. Fred Rosenbaum
Assistant Examiner—Gene B. Kartchner
Attorney, Agent, or Firm—Cushman, Darby & Cushman

[57] ABSTRACT

A completely flexible bronchoscopic needle assembly for use with a fiberoptic bronchoscope includes a flexible catheter having a hollow sampling needle rigidly and coaxially fixed to the distal end thereof. The sampling needle defines a lateral opening rearwardly of a cutting edge so as to permit an increased quantity of tissue sample to pass through the lateral opening and into the hollow sampling needle. The rearward portion of the lateral opening is defined by a lateral cutting edge to cut into the surrounding tissues so as to obtain a sample therefrom when the sampling needle is forcibly advanced into the tissue. The forward portion of the lateral opening is defined by a gradual inwardly sloped surface which prevents the tissue from being cut when the sampling needle is withdrawn from the tissue. An inner needle is slidably received within the hollow of the sampling needle for moements between an advanced position and a retracted position so as to effectively mask the forward and lateral cutting edges of the sampling needle when in its advanced position while yet permitting cutting of tissue when in its retracted position.

18 Claims, 6 Drawing Figures

FLEXIBLE BRONCHOSCOPIC NEEDLE ASSEMBLY

CROSS-REFERENCE TO RELATED APPLICATIONS

Further insight into needle assemblies relating to the present invention may be gained by reference to U.S. application Ser. No. 472,603 filed Mar. 7, 1983, now U.S. Pat. No. 4,532,935 which is a continuation-in-part of Ser. No. 438,245 filed Nov. 1, 1982 which, in turn, is a continuation-in-part of application Ser. No. 260,602 filed May 6, 1981 (now abandoned), the disclosure of each application being expressly incorporated hereinto by reference.

FIELD OF INVENTION

The present invention relates generally to a flexible bronchoscopic needle assembly for use with a flexible bronchoscope so as to obtain tissue samples from a patient. More particularly, the present invention is directed to a flexible bronchoscopic needle assembly whereby a rigid hollow sampling needle is coaxially fixed to a distal end of a flexible catheter, the sampling needle including a lateral opening in the side wall thereof rearwardly of a forward cutting edge so that the lateral opening will permit an additional quantity of tissue sample to pass therethrough and into the hollow portion of the sampling needle.

BACKGROUND AND SUMMARY OF THE INVENTION

In the above-noted related applications, completely flexible bronchoscopic needle assemblies are disclosed wherein relatively non-invasive biopsy procedures can be performed utilizing the needles in combination with a fiberoptic bronchoscope. The attending physician inserts the bronchoscope into a predetermined one of the patient's natural orifices depending upon the particular organ desired to be biopsied. Thereafter, a needle assembly in accordance with the invention described in the above-noted related applications is slideably inserted into a receiving passageway of the bronchscope. The needle is urged into the tissue of the patient by a stabbing force exerted on the proximal end thereof (i.e. the end on the exterior of the patient's body) after the tubular needle portion comes into the bronchoscope's field of view. The bronchoscope enables the attending physician to accurately position the needle and to penetrate the exact location of the desired organ due to the viewing capabilities provided thereby. The present invention is directed to improvements in the needle assemblies of the types generally disclosed in my related applications referenced above.

Heretofore, when biopsies were desired to be taken of the lymph nodes, for example, so as to aid in the diagnosis of carcinoma, the prior techniques would all typically utilize a substantially rigid needle and penetrate the body via percutaneous entry. For example, U.S. Pat. Nos. 3,630,192 and 3,628,524 each to Jamshidi disclose prior art biopsy needles suitable for percutaneous entry. It has been proposed via U.S. Pat. No. 4,249,541 to Pratt that a flexible biopsy instrument can be utilized in combination with a fiberoptic bronchoscope. One problem with Pratt's needle device, however, is that no protective structures are provided when the needle assembly is inserted through the fiberoptic bronchoscope so as to protect, not only the fiberoptic bronchoscope but also the patient from inadvertant damage due to the sharp edge of the needle until such time as the physician desires to penetrate the patient's internal organ tissue.

In order to provide accurate biopsies, a sufficient quantity of biopsy tissue material must be obtained so that adequate testing can be performed. In order to obtain a greater quantity of tissue samples, it is of course conceivable to utilize a biopsy needle having a relatively large lumen. However, the use of large-lumen biopsy needles is disadvantageous since a fairly large puncture wound will be necessary if a biopsy is to be taken, for example, of tissue behind the bronchial walls of a patient such that excessive bleeding may result when the needle is withdrawn.

The present invention overcomes such problems by providing a flexible bronchoscopic needle having an elongated flexible catheter to which a rigid hollow sampling needle is coaxially fixed at the distal end thereof. An increased quantity of tissue sample can be obtained in accordance with the present invention by the provision of a lateral opening in the sampling needle. The lateral opening is defined by a rearward lateral cutting edge which functions so as to cut into the tissue when the sampling needle is forcibly advanced and a gradual inwardly slopped surface defined forwardly of the lateral cutting edge which functions so as to prevent the tissue from being cut when the sampling needle is withdrawn. The distal end of the sampling needle also includes a bevelled forward cutting edge which is disposed in a plane substantially transverse to the sampling needle. Accordingly, tissue cutting functions are provided not only by the forward bevelled cutting edge but also by the lateral cutting edge of the lateral opening. Moreover, such cutting functions are effective only when the sampling needle is advanced into tissue such that upon repetitive advancement and withdrawal of the sampling needle, the cut tissue will be forcibly accumulated in the hollow of the sampling needle. In such a manner, the structures of the present invention permit an increased quantity of tissue samples to be obtained.

A further aspect of the invention relates to the means by which the lateral cutting edge is effectively masked so as to prevent it from cutting into tissue. According to the present invention therefore there is also provided an inner needle which is slideably reciprocally receivable within the hollow of the sampling needle and is moveable between an advanced position wherein the inner needle adjacently blocks the lateral opening and a retracted position wherein the inner needle is rearwardly withdrawn from the lateral opening to permit passage of tissue therethrough. Preferably, the inner needle at its distal end defines a sharp surface which projects outwardly from the forward cutting edge of the sampling needle when the inner needle is in its advanced position.

The sharp surface of the inner needle thus initially penetrates the bronchial walls of a patient, for example, so as to provide a small-sized pilot incision of sorts. The larger-sized sampling needle will thus be forced through the pilot incision without further cutting action by virtue of the masked relationship of the forward cutting edge. Similarly, the inner needle will mask the lateral cutting edge so that no cutting functions of the bronchial wall other than the small pilot incision will be initially effected while yet permitting the sampling needle to be extended through the bronchial wall and into the tissue therebeyond. Upon retraction of the inner needle, the forward cutting edge and the lateral cutting edge of the sampling needle are thus effectively unmasked thereby permitting their cutting functions to be performed upon forcible advancement of the sampling needle into the tissue to be biopsied.

As such, the structures of the present invention prevent large-sized incisions in a patient's bronchial walls, for example, while yet permitting a larger quantity of sample tissue to be obtained. The above advantages of the present invention, as well as others, will become more clear to the reader after careful consideration is given to the detailed description of the preferred exemplary embodiments thereof which follows.

BRIEF DESCRIPTION OF THE ACCOMPANYING DRAWINGS

Reference will be hereinafter made to the accompanying drawings wherein like reference numerals throughout the various Figures denote like structural elements and wherein.

DETAILED DESCRIPTION OF THE PREFERRED EXEMPLARY EMBODIMENTS OF THE PRESENT INVENTION

Figure 1:
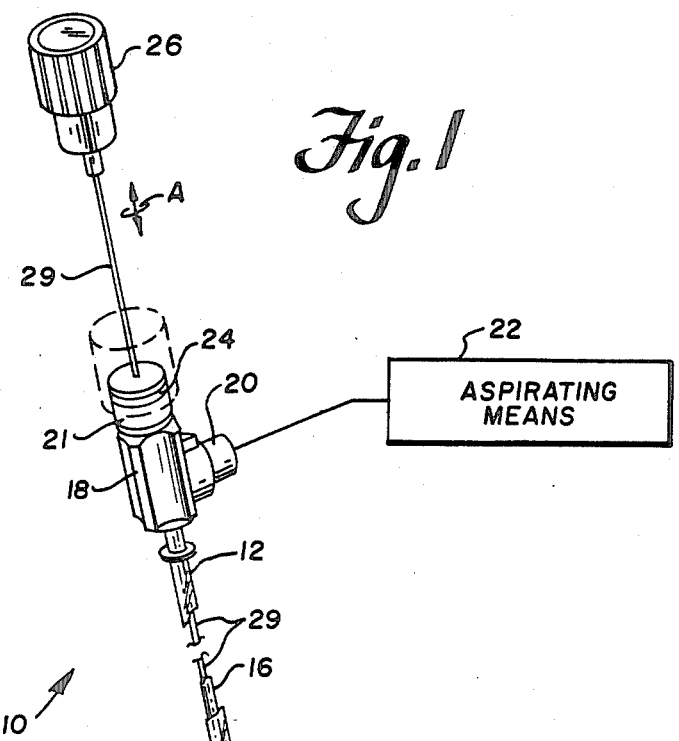
FIG. 1 is a perspective view of the needle assembly in accordance with the present invention.

As shown in FIG. 1, the biopsy needle assembly 10 generally includes a flexible elongate catheter 12 having a rigid elongate hollow sampling needle 14 of between 1.0 to 1.5 cm in length rigidly and coaxially fixed to the distal end of catheter 12. A flexible stylette (preferably formed of fine gauge stainless steel wire) is slidably received within catheter 12 and preferably includes an inner needle 16 attached to its distal end.

The proximal end of needle assembly 10 preferably includes a conventional two-directional leur lock 18, one of the directional nipples 20 being provided to accept a conventional asperating means 22, such as, the syringe assembly disclosed in co-pending U.S. application Ser. No. 438,245 filed Nov. 1, 1982. The other directional nipple 21 of leur lock 18 defines engagement threads 24 for removably threadably coupling cap 26 thereto so as to permit the inner needle 16 to be extended beyond the cutting edge 28 of sampling needle 14 (i.e. as shown in dashed line in FIG. 1). The cap 26 is thus connected to the proximal end of the stylette 29 so as to permit manual reciprocal movements thereof (noted by arrow "A" in FIG. 1) and thus to reciprocally move the inner needle 16 between its advanced position (noted in dashed line in FIG. 1) and its retracted position (noted by solid line in FIG. 1), the purpose of which will become more clear from the discussion below.

Figure 2:
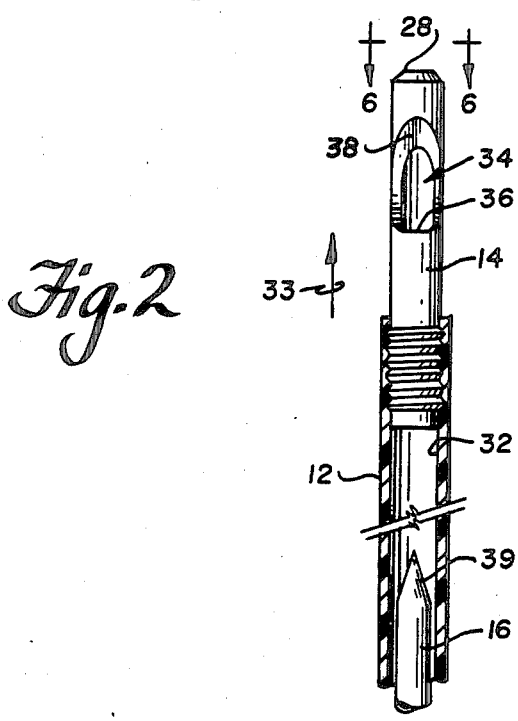
FIG. 2 is an elevational view of the distal end of one embodiment of the needle assembly of the present invention shown with the inner needle in a retracted position.
Figure 3:
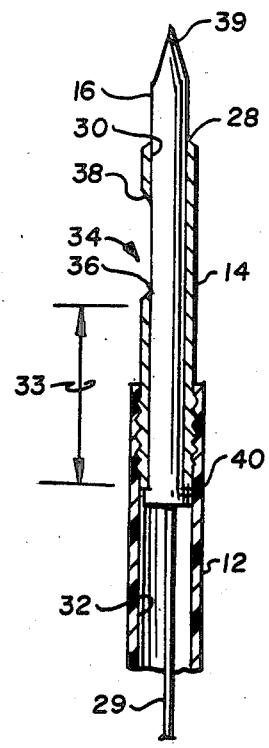
FIG. 3 is a cross-sectional elevational view of the FIG. 2 needle assembly but showing the inner needle in an extended position.
Figure 6:
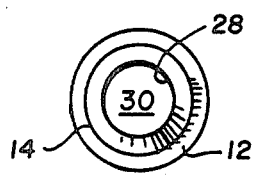
FIG. 6 is a plan view of the forward cutting edge of the sampling needle taken along lines 6—6 in both FIGS. 2 and 4.

One embodiment of the sampling needle 14 and inner needle 16 is shown in accompanying Figures 2 and 3. As can be seen, the sampling needle 14 at its forward end thereof defines an inwardly bevelled cutting edge 28 which is disposed in a plane substantially perpendicular to the elongate axis of sampling needle 14 so as to provide a substantially circular cutting edge when viewed in plan (see FIG. 6). The hollow 30 of the needle 14 is thus in communication with the inner cavity 32 of the catheter 12. When the sampling needle 14 is forcibly advanced (arrow 33) into tissue to be biopsied, the cutting edge 28 will cut portions of the desired tissue and such cut tissue portions will then be transferred to the hollow 30 of needle 14 and accumulate generally in the proximal portion 33 thereof.

The sampling needle 14 defines a lateral opening 34 in communication with the hollow 30 of needle 14 so as to also permit biopsy tissue samples to pass therethrough and accumulate in proximal portion 33. Lateral opening 34 is defined at its rearward portion by means of a lateral cutting edge 36 which serves to cut into the surrounding tissue only when the sampling needle 14 is forcibly advanced (arrow 33) into the tissue. Lateral opening 34 at its forward portion thereof is defined by a gradual inwardly tapered surface 38 which serves to prevent the surrounding tissue from being cut when the sampling needle 14 is withdrawn from the tissue (i.e., in a direction opposite to arrow 33). In such a manner, repeated advancement and withdrawal of the sampling needle 14 relative to surrounding tissue causes edge 36 to repeatedly cut samples of the tissue so that such cut sample tissues can be passed through opening 34 and then on to the proximal portion 33 of sampling needle 14. As can be appreciated, repetitive advancement of needle 14 will cause edges 28 and 36 to cut tissue samples thereby advantageously compacting tissue samples accumulated in proximal portion 33. Compaction of accumulated tissue within proximal portion 33 thus permits an increased quantity of sample tissue to be obtained.

The inner needle 16 preferably defines a sharp conical point 39 which extends outwardly beyond forward cutting edge 28 of sampling needle 14 when inner needle 16 is in its advanced position as shown in FIG. 3. A limit member 40 integrally provided at the proximal end of inner needle 16 abuts against the proximal end of sampling needle 14 to thus establish the advanced position of inner needle 16. Preferably, needle 16 in the embodiment of FIGS. 2 and 3 is solid but a tubular needle could also be used, if desired.

When inner needle 16 is in its advanced position, it will be noted that needle 16 is in substantial sliding contact adjacent to edges 28 and 36. Such adjacent sliding contact of needle 16 relative to the forward cutting edge 28 and the lateral cutting edge 36 effectively masks the tissue-cutting functions of the latter so as to prevent surrounding tissue from being cut thereby. The sharp point 39 of inner needle 16 thus serves to provide a pilot incision in the bronchial wall, for example, of a patient such that the sampling needle 14 can be inserted through the pilot incision without removing a substantially greater amount of the bronchial wall than is absolutely necessary. The sampling needle 14 can then be forcibly advanced into the tissue behind the bronchial wall without causing excessive bleeding.

Once the sampling needle 14 is in position such that the tissue behind the bronchial wall has at least been initially penetrated, the inner needle 16 is withdrawn to its retracted position within the cavity 32 of catheter 12 (as shown in FIG. 2) by manual movement of cap 26 to its position shown in solid line in FIG. 1. When the inner needle 16 is in its retracted position, the forward cutting edge 28 and lateral cutting edge 36 are thus unmasked thereby permitting the physician to advance (arrow 33) the needle 14 forcibly into the tissue to be biopsied so that the cutting edges 28 and 36 can obtain sample tissue therefrom. However, upon withdrawal of the sampling needle 14 from the tissue and through the bronchial wall, the gradual taper of surface 38 defining the forward portion of lateral opening 34 prevents the bronchial wall from being further cut thereby also avoiding excess bleeding thereof.

Figure 4:
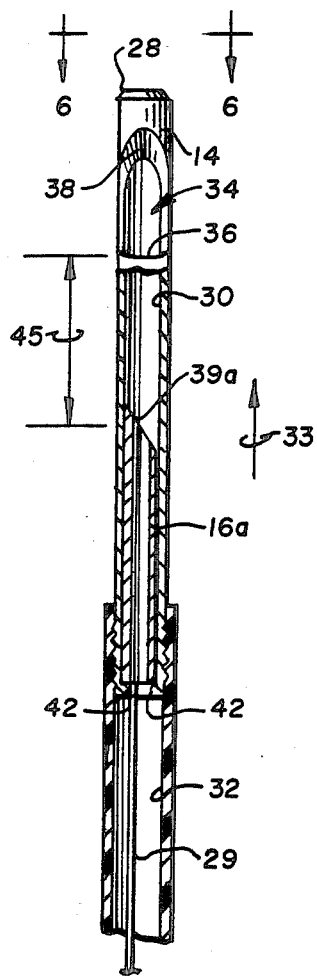
FIG. 4 is a elevational view, partially in section, of another embodiment of the needle assembly of the present invention shown with the inner needle in a retracted position.
Figure 5:
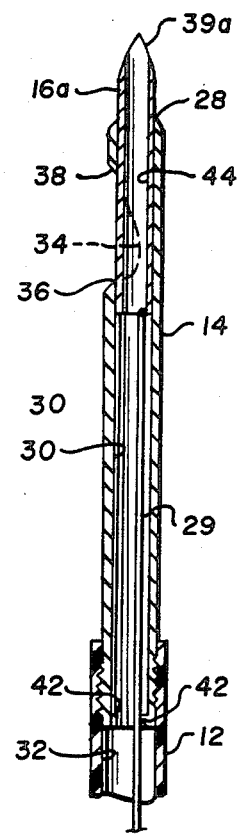
FIG. 5 is a cross-sectional elevational view of the needle assembly shown in FIG. 4 with the inner needle in an extended position.

Another embodiment of the present invention is shown in accompanying FIGS. 4 and 5 and is similar in most respects to the embodiment of the invention shown in FIGS. 2 and 3 described immediately above. That is, the sampling needle 14 will include a forward cutting edge 28, lateral opening 34 having its rearward portion defined by the lateral cutting edge 36 and its forward portion defined by the gradual inwardly tapered surface 38 so as to provide functions similar to that discussed above. Different, however, are the provisions or a bevelled edge 39a on inner needle 16a and the tubular nature of needle 16a.

The embodiment of the invention shown in FIGS. 4 and 5 however permits the inner needle 16 to only be movable within the hollow 30 of sampling needle 14. In this regard, retraction-limiting members 42 are provided at an extreme proximal portion of sampling needle 14 and project towards one another so as to restrict the cross-sectional dimension of the hollow 30 of sampling needle 14. Accordingly, when the stylette 29 is withdrawn by manipulation of cap 26, the inner needle 16a rigidly fixed thereto by means of suitable weld, epoxy or other like securing means is retracted within hollow 30 of sampling needle 14 until its proximal end abuts against retraction limiting members 42. While in its retracted position (as shown in FIG. 4), needle 16a, by virtue of its lesser axial length as compared to needle 14, thus unmasks the forward cutting edge 28 and lateral cutting edge 36 so that their tissue-cutting functions as described above can be realized. When the inner needle 16a is moved into its advanced position (as shown in FIG. 5), the forward cutting edge 28 and lateral cutting edge 36 will be masked in a manner similar to the embodiment described above with reference of FIGS. 2 and 3.

In a manner similar to that described above, an increased quantity of tissue sample will be compacted generally in the intermediate region 45 of needle 14 between bevelled edge 39a and cutting edge 36. Since needle 16a in the embodiment of FIGS. 4 and 5 is tubular, some compacted mass of tissue sample may also be accumulated therein. Reverse operation of aspirating means 22 so as to force a saline solution to, for example, to the distal end of assembly 10 will easily cleanse needles 14 and 16 after the biopsy procedure is completed thereby also permitting collection of the tissue samples.

By way illustration, the needle 14 of the FIGS. 4 and 5 embodiment is between 1.0 to 1.5 cm in axial length while the axial lengths and lateral opening 34 and inner needle 16 are each about 0.5 cm. Thus, intermediate region 45 will be about 0.5 cm in axial length to provide an accumulation volume of efficient proportions for the tissue samples.

Preferably, the embodiment of the invention shown in FIGS. 4 and 5 will have suitable biasing structure as described in co-pending application Ser. No. 472,603 filed Mar. 7, 1983 now U.S. Pat. No. 4,532,935 so as to ensure initial insertion rigidity of inner needle 16 relative to sampling needle 14 to thus ensure that inadvertant retraction of inner needle 16a is prevented.

Accordingly, while the present invention has been herein described and was presently conceived to be the most preferred embodiments thereof, those in the art will appreciate the many modifications may be made hereof, which modifications shall be accorded the broadest scope of the appended claims so as to encompass all equivalent assemblies, structures, and/or devices.

I claim:

1. A flexible bronchoscopic needle assembly for use with a flexible brochoscope to obtain tissue samples from a patient, said needle assembly comprising:
   an elongated flexible catheter having proximal and distal ends and defining an interior cavity therebetween; and
   a rigid hollow sampling needle rigidly and coaxially fixed to said catheter distal end, said sampling needle including means defining an opening at the distal end and a forward cutting edge about said opening means for cutting into desired tissue to obtain sample therefrom, the hollow of said sample needle being in communication with said interior cavity of said catheter;
   said hollow sampling needle also including a side wall and means defining an exposed lateral opening positioned rearwardly of said distal end within the side wall which is in communication with the hollow interior of said sampling needle to also permit tissue samples to pass through said lateral opening and into the hollow sampling needle whereby samples can pass into and through the hollow needle and into the elongated flexible catheter without removal of the catheter from the bronchoscope.

2. A needle assembly as in claim 1 wherein said lateral opening-defining means includes lateral cutting edge means for cutting into the tissue to obtain a sample therefrom when said sampling needle is forcibly advanced into the tissue.

3. A needle assembly as in claim 2 wherein said lateral opening-defining means further includes means defining a surface forwardly of said lateral cutting edge means for preventing tissue from being cut when said sampling needle is withdrawn from the tissue, said surface and said cutting edge together establishing said lateral opening.

4. A flexible needle assembly as in claim 2 further comprising inner needle means slidably received within the hollow interior of said sampling needle, and means permitting the manual movement of said inner needle means between (i) an advanced position wherein said inner needle means adjacently blocks said lateral opening to effectively mask said lateral cutting edge means thereof, thereby to prevent said lateral cutting edge means from cutting into the tissue when said sampling needle is forcibly advanced into the tissue, and (ii) a retracted position wherein said inner needle means is rearwardly withdrawn from said lateral opening to permit said lateral cutting edge means to cut tissue when forcibly advanced into the tissue and thus to permit passage of the cut tissue therethrough.

5. A flexible needle assembly as in claim 4 wherein said inner needle means defines a distal sharp surface which projects beyond said forward cutting edge means when said inner needle means is in said advanced position to aid in penetrating the tissue.

6. A flexible needle assembly as in claim 4 wherein said means permitting manual movement of said inner needle means includes a flexible stylette having one end disposed exteriorly of said catheter proximal end and an opposite end rigidly attached to said inner needle means.

7. A flexible needle assembly as in claim 6 wherein said means permitting manual movement of said inner needle means includes a cap fixed to said one end and locking means for removably locking said cap to said catheter proximal end to thereby removably lock said inner needle means in said advanced position.

8. A flexible needle assembly as in claim 4 wherein said hollow sampling needle includes retraction limit means projecting into the hollow of said sampling needle for establishing said retracted position of said inner needle means.

9. A flexible needle assembly as in claim 8 wherein said inner needle means is tubular.

10. A flexible needle as in claim 4 wherein said inner needle means includes advancement limit means which abuts against a portion of said sampling needle for establishing said advanced position of said inner needle means.

11. A flexible needle assembly as in claim 10 wherein said inner needle means is solid.

12. A flexible needle assembly as in claim 1 wherein said forward cutting edge is circular as viewed in plan and is disposed in a plane transverse to said sampling needle.

13. A needle assembly as in claim 1 where in said lateral opening defining means has a forward portion adjacent said forward cutting edge and a rearward portion adjacent said catheter distal end.

14. A needle assembly as in claim 13 wherein said rearward portion comprises cutting edge means for cutting tissue as said needle is advanced into the tissue to be sampled.

15. A needle assembly as in claim 14 wherein said forward portion comprises a gradually tapering surface to prevent tissue cutting as said needle is withdrawn from the tissue.

16. A flexible needle as in claim 10 wherein said inner needle means is hollow.

17. A flexible needle as in claim 16 wherein said inner needle means further includes a flexible stylette having one end disposed exteriorly of the catheter proximal end and an opposite end rigidly attached to said inner needle means.

18. A flexible needle as in claim 17 wherein said stylette is spaced from the interior of the catheter along the length thereof.

* * * * *